(12) United States Patent
Pandey et al.

(10) Patent No.: US 10,253,066 B2
(45) Date of Patent: Apr. 9, 2019

(54) PROCESS FOR PURIFICATION OF CARFILZOMIB

(71) Applicant: Fresenius Kabi Oncology Limited, New Delhi (IN)

(72) Inventors: Maneesh Kumar Pandey, Gurgaon (IN); Raj Narayan Tiwari, Gurgaon (IN); Sarbjot Singh Sokhi, Gurgaon (IN); Govind Singh, Gurgaon (IN); Saswata Lahiri, Gurgaon (IN); Walter Cabri, Milan (IT)

(73) Assignee: FRESENIUS KABI ONCOLOGY LIMITED, New Delhi (IN)

( * ) Notice: Subject to any disclaimer, the term of this patent is extended or adjusted under 35 U.S.C. 154(b) by 0 days.

(21) Appl. No.: 15/532,718

(22) PCT Filed: Dec. 1, 2015

(86) PCT No.: PCT/IB2015/059239
§ 371 (c)(1),
(2) Date: Jun. 2, 2017

(87) PCT Pub. No.: WO2016/088031
PCT Pub. Date: Jun. 9, 2016

(65) Prior Publication Data
US 2018/0002377 A1 Jan. 4, 2018

(30) Foreign Application Priority Data
Dec. 2, 2014 (IN) .......................... 3510/DEL/2014

(51) Int. Cl.
*C07K 1/02* (2006.01)
*A61P 35/00* (2006.01)
*C07K 5/103* (2006.01)

(52) U.S. Cl.
CPC .............. *C07K 5/101* (2013.01); *A61P 35/00* (2018.01); *C07K 1/02* (2013.01); *C07K 5/1008* (2013.01)

(58) Field of Classification Search
CPC ......... C07K 1/02; C07K 5/1008; C07K 5/101
See application file for complete search history.

(56) References Cited

U.S. PATENT DOCUMENTS

| 9,315,542 B2* | 4/2016 | Phiasivongsa ........... C07K 5/08 |
| 2015/0166601 A1* | 6/2015 | Morgan ............... C07K 5/1024 514/19.6 |

FOREIGN PATENT DOCUMENTS

| CN | 103641890 | 3/2014 |
| WO | 2009/045497 | 4/2009 |

* cited by examiner

*Primary Examiner* — Marcela M Cordero Garcia
(74) *Attorney, Agent, or Firm* — Hylton-Rodic Law PLLC

(57) ABSTRACT

The present invention relates to a process for the purification of Carfilzomib of Formula I that reduces the level of an acetamide impurity of Formula II preferably below 0.10 wt %.

Formula I

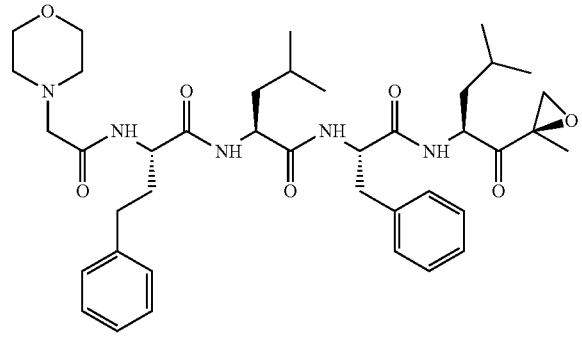

Formula II

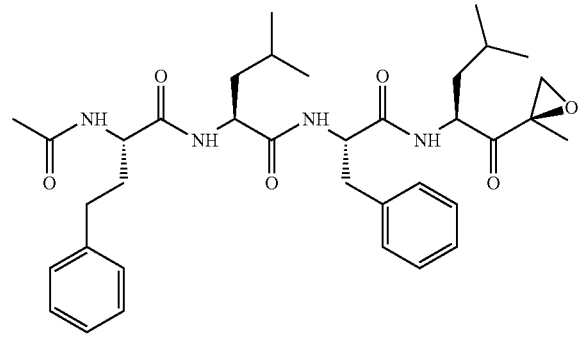

13 Claims, 1 Drawing Sheet

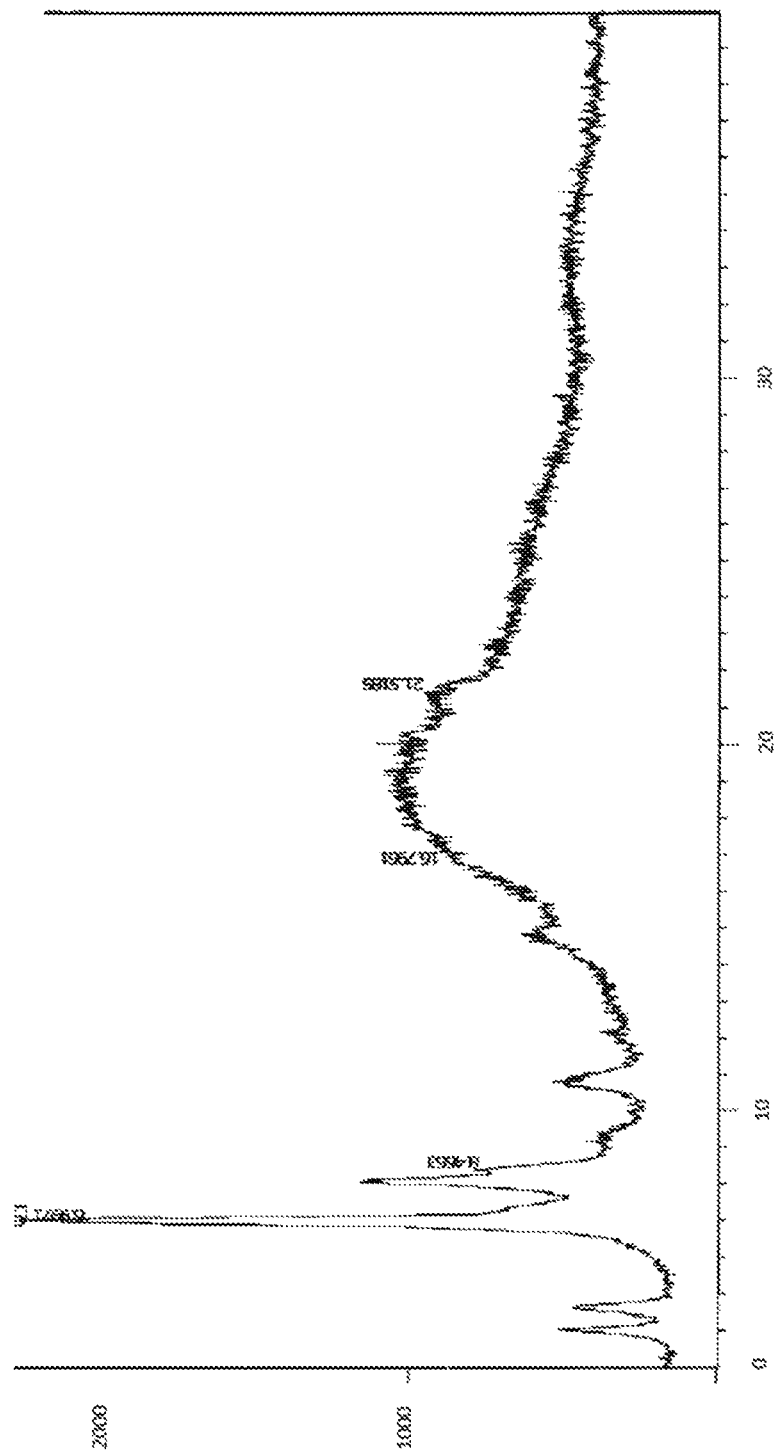

PROCESS FOR PURIFICATION OF CARFILZOMIB

CROSS REFERENCE TO RELATED APPLICATIONS

This application is a U.S. national stage application under 35 U.S.C. § 371 of International Application No. PCT/IB2015/059239, filed on Dec. 1, 2015, which claims priority to Indian Application No. 3510/DEL/2014, filed on Dec. 2, 2014, the contents of which are hereby incorporated by reference herein in their entirety.

FIELD OF THE INVENTION

The present invention relates to a process for purifying Carfilzomib and, in particular reducing an acetamide impurity generally formed during synthesis of Carfilzomib.

BACKGROUND OF THE INVENTION

Carfilzomib, (2S)—N-{(1S)-1-Benzyl-2-[((1S)-3-methyl-1-{[(2R)-2-methyloxiran-2-yl]carbonyl}butyl)amino]-2-oxoethyl}-4-methyl-2-({(2S)-2-[(morpholin-4-ylacetyl)amino]-4-phenylbutanoyl}amino)pentanamide, is represented by the Formula

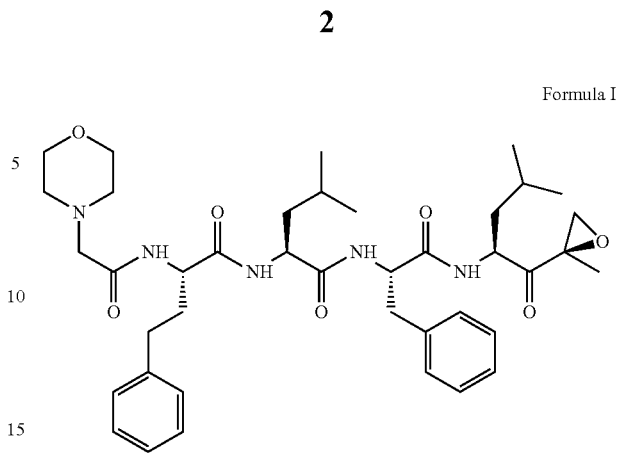

Formula I

Carfilzomib (CFZ, marketed under the tradename Kyprolis, Onyx Pharmaceuticals, Inc.) is a tetrapeptide epoxyketone and a selective proteasome inhibitor. It is an analog of epoxomicin.

The U.S. Food and Drug Administration (FDA) approved it on 20 Jul. 2012 for use in combination with lenalidomide and dexamethasone in patients with relapsed multiple myeloma, who have received one to three prior lines of therapy. It is also indicated for use in patients with multiple myeloma who have received at least two prior therapies, including treatment with bortezomib and an immunomodulatory therapy and have demonstrated disease progression on or within 60 days of completion of the last therapy. Carfilzomib as represented by Formula I is first disclosed in WO 05105827/U.S. Pat. No. 7,417,042.

U.S. Pat. Nos. 7,417,042; 7,232,818 and 8,207,297 describe a process for the preparation of Carfilzomib. The Scheme is summarized below in scheme 1:

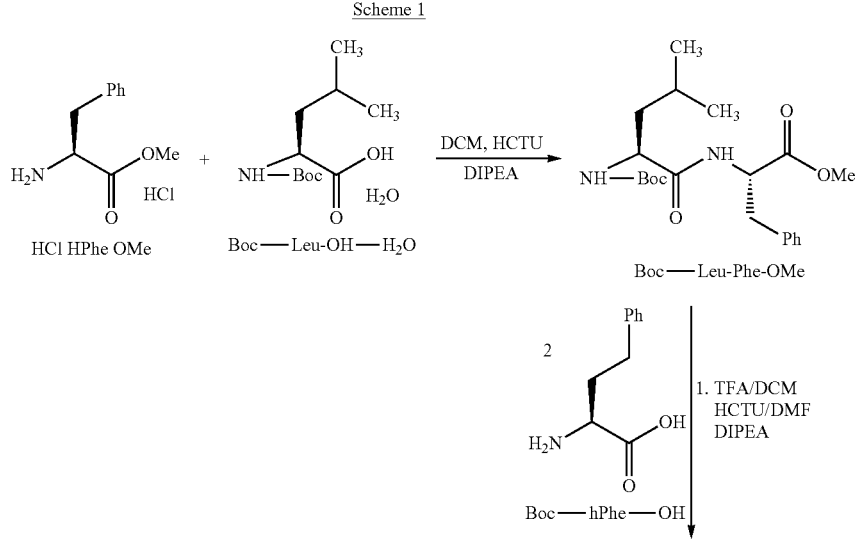

Scheme 1

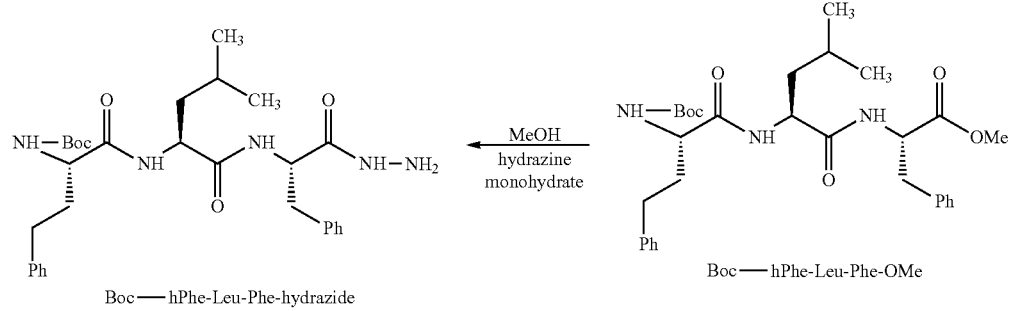

Boc—hPhe-Leu-Phe-OMe

MeOH
hydrazine monohydrate

Boc—hPhe-Leu-Phe-hydrazide
C

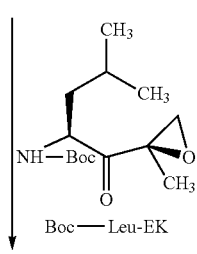

Boc—Leu-EK

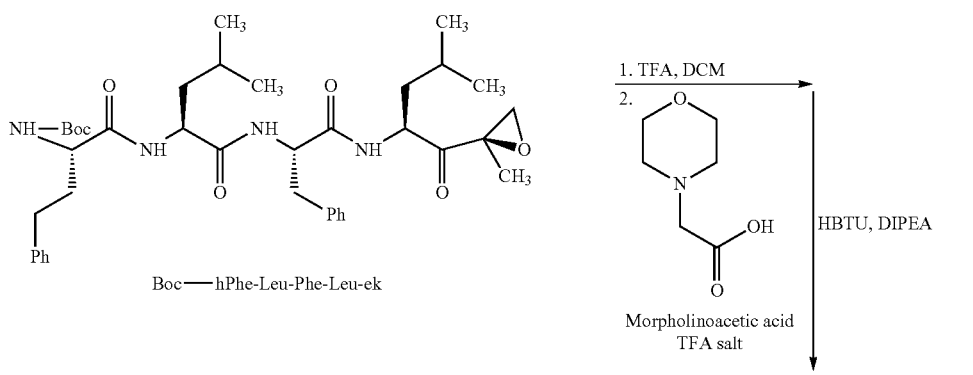

Boc—hPhe-Leu-Phe-Leu-ek

1. TFA, DCM
2. Morpholinoacetic acid TFA salt

HBTU, DIPEA

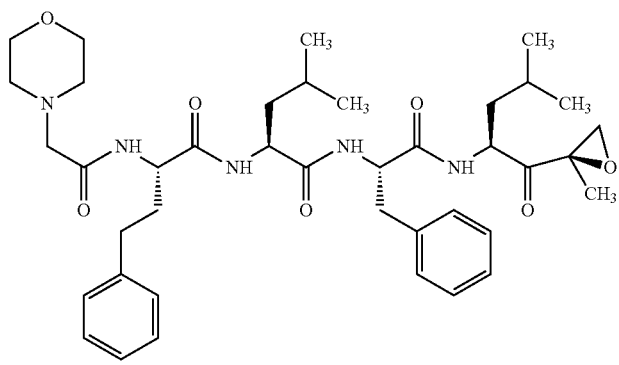

Carfilzomib wherein, "Boc" means tert-butoxycarbonyl; Bz and Bn means benzoyl and benzyl groups respectively; MeCN means acetonitrile; TFA means trifluoroacetic acid; DMF means dimethyl formamide; DCM means Dichloromethane; DIEA means diisopropyl ethyl amine; HOBT means hydroxyl benzatriazole; PyBop means benzotriazol-1-yl-oxytripyrrolidinophosphonium hexafluorophosphate. The Carfilzomib thus obtained therein was crystallized in presence of methanol and water, and isolated by filtration.

Yet another process is described in *Nature of Pharmacophore*; Micheal Screen, et al. *J. Biol. Chem.* 2010, 285: 40125-40134. The Scheme is summarized below in Scheme 2.

Scheme 2
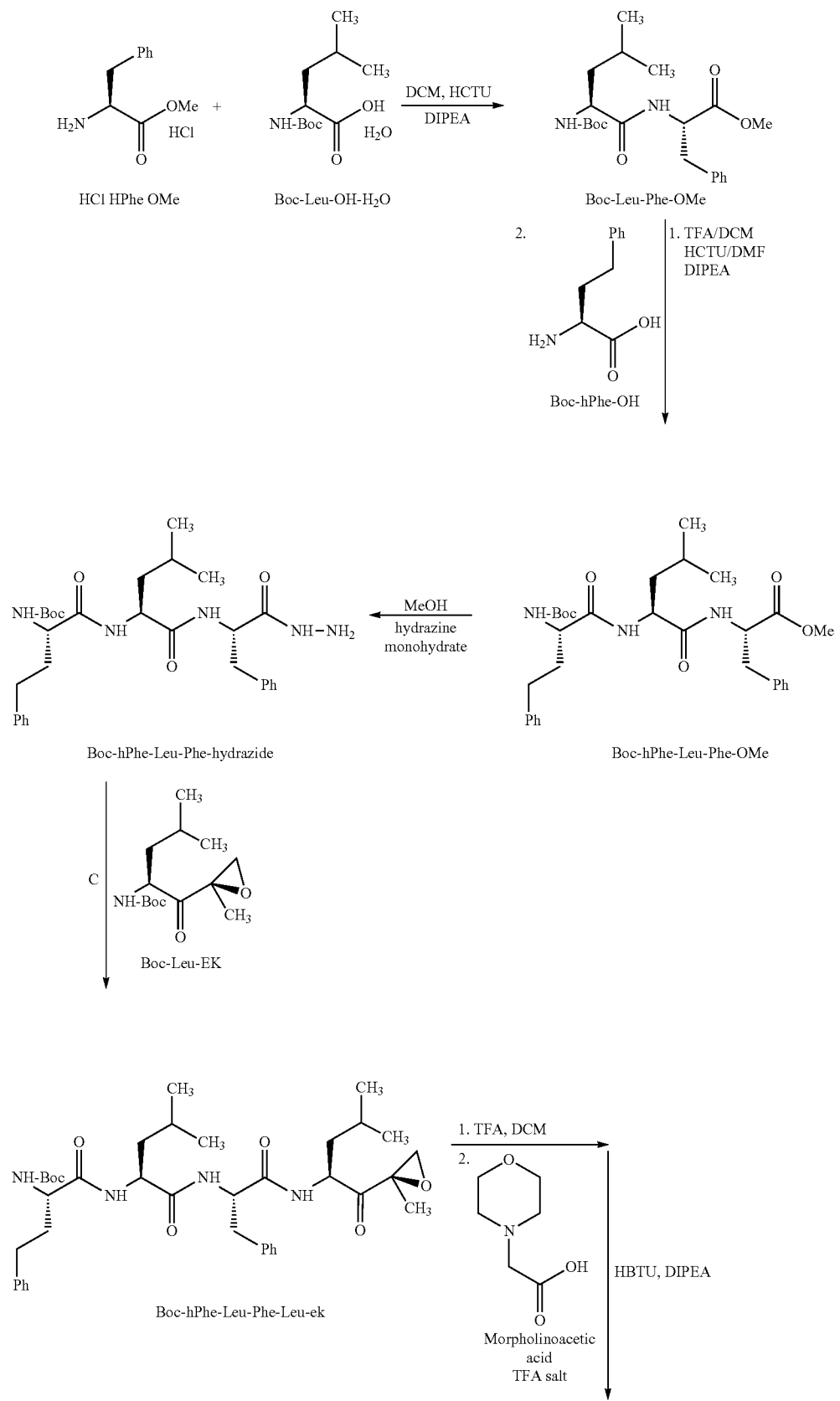

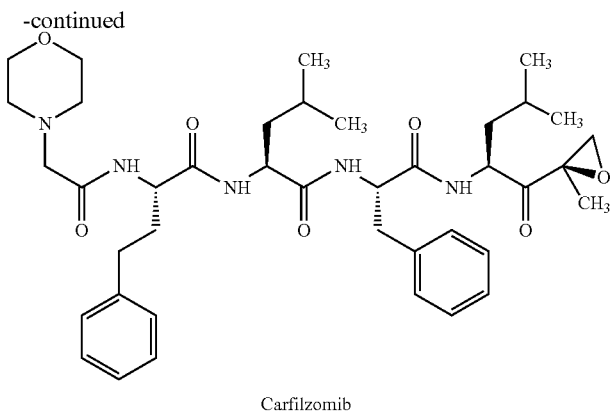

Carfilzomib wherein, "HBTU" means N,N,N',N'-Tetramethyl-O-(1H-benzotriazol-1-yl)uronium hexafluorophosphate. The Carfilzomib thus obtained therein was purified by column chromatography.

U.S. Pat. No. 8,367,617 discloses a crystalline form of Carfilzomib, salts of Carfilzomib, wherein the salt counterion is selected from citrate, tartrate, trifluoroacetate, methanesulfonate, toluenesulfonate, chloride, and bromide.

Unfortunately, an acetamide impurity of Formula II,

Formula II

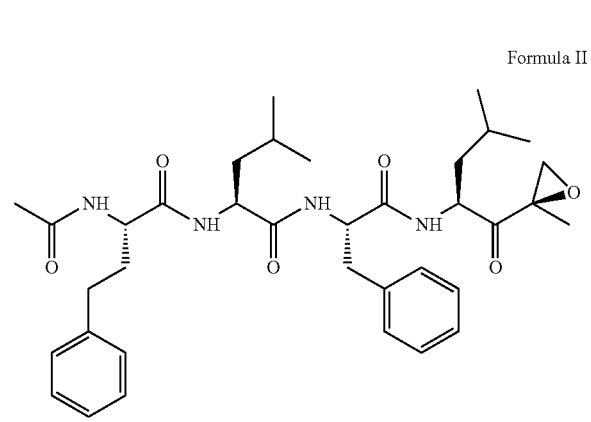 [SMILES: CC(=O)N[C@@H](CCc1ccccc1)C(=O)N[C@@H](CC(C)C)C(=O)N[C@@H](Cc1ccccc1)C(=O)N[C@@H](CC(C)C)C(=O)[C@@]1(C)CO1]

is inevitably formed in prior art processes described in U.S. Pat. Nos. 7,417,042; 7,232,818 and 8,207,297 and this impurity is difficult to separate from the desired end product. Even by using different purification methods including recrystallization, the impurity remains in an undesired amount.

Thus, there still remains the need to formulate efficient and economical purification procedure especially, for use on an industrial scale.

The inventors have now discovered a process for purification of Carfilzomib by reducing the amount of the acetamide impurity of formula II, hereinafter referred as acetamide impurity without using potential time consuming crystallization and recrystallization techniques or expensive chromatography. Rather the inventors have found that the best way to remove this impurity is by formation of suitable salt of Carfilzomib with weak acid. Surprisingly it is found, that the use of oxalate salt of Carfilzomib as an intermediate within the process of the present invention leads to superior results. Finally this oxalate salt of Carfilzomib is converted to Carfilzomib by reacting it with a base, wherein the Carfilzomib thus obtained has less than 0.10 wt % of acetamide impurity.

SUMMARY OF THE INVENTION

To provide an improved commercially viable process for the purification of Carfilzomib of Formula I, Formula I the process of present invention is an easy and cost effective process to implement on industrial scale.

Another objective of present invention is to provide a process for purification of Carfilzomib of Formula I to reduce an acetamide impurity of Formula II Formula II to below 0.10 wt % in the final Carfilzomib.

Yet another objective of the present invention is to avoid column/flash chromatography for isolation and purification of Carfilzomib.

Further objective of the present invention is to produce oxalate salt of Carfilzomib of Formula III, Formula III

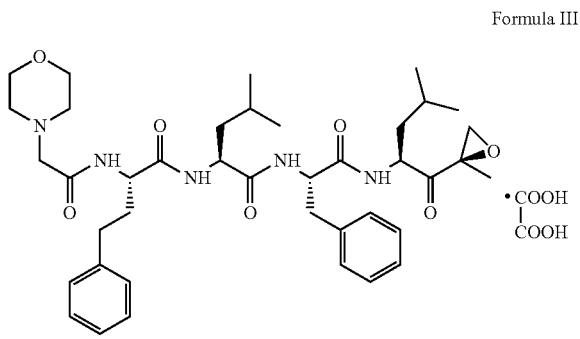

which can be used as an intermediate in the preparation of Carfilzomib to reduce the acetamide impurity of formula (II) below 0.10 wt % in the final Carfilzomib.

Thus a method for purification of Carfilzomib of Formula I is developed as depicted in reaction Scheme 3.

Scheme 3

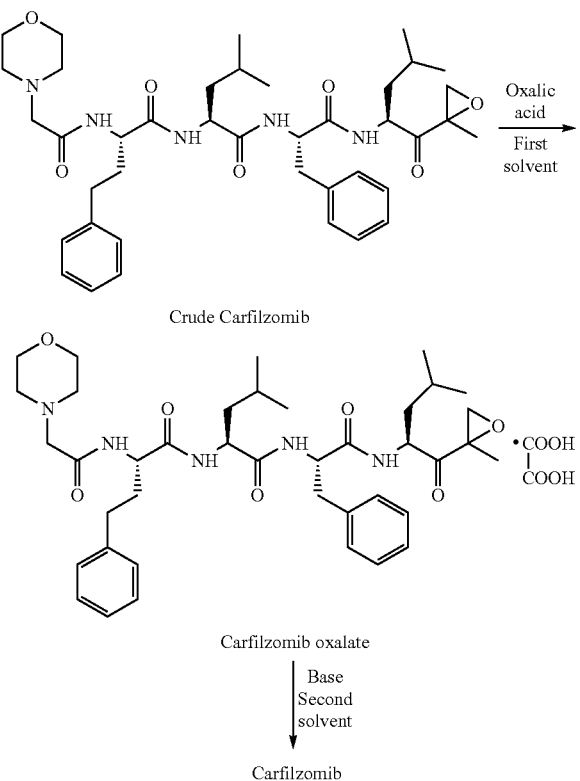

According to the present invention, the purification of Carfilzomib of Formula I from acetamide impurity of Formula II comprises the steps of:
(i) dissolving crude Carfilzomib in a first solvent and adding oxalic acid to form Carfilzomib oxalate;
(ii) precipitating said Carfilzomib oxalate;
(iii) reacting said Carfilzomib oxalate with a base in a second solvent to obtain the Carfilzomib.

Crude Carfilzomib contains undesired impurities including acetamide impurity of formula (II).

By way of examples, the benefits of the invention are demonstrated in Table 1. According to batch no. 1, the purification via the oxalate salt of carfilzomib leads to final product with a purity which is at least about 5 times better than by the use of other salts. In detail: The Carfilzomib purified by the process of the invention has a content of the acetamide impurity of less than 0.10 wt %. Whereas the best of the comparative batches using other salts leads to rest of the acetamide impurity of 0.21 wt % or worse.

The acetamide impurity is measured by high performance liquid chromatography (HPLC) technique using C18 column and the results are summarized herein below in Table-1.

TABLE 1

| | Purification of Carfilzomib | | |
|---|---|---|---|
| Batch. No. | Carfilzomib Salts | Acetamide Impurity wt % (Input, crude Carfilzomib) | Acetamide Imp. wt % (After De-Salt) i.e pure Carfilzomib |
| 1 | Purification via Oxalate salt | 0.37 | 0.04 |
| 2 | Purification via Maleate salt | 0.37 | 0.21 |
| 3 | Purification via Succinate salt | 0.37 | 0.35 |
| 4 | Purification via Citrate salt | 0.37 | 0.33 |

DESCRIPTION OF THE ACCOMPANYING DRAWINGS

FIG. 1: X-ray powder diffraction pattern (XRPD) of Carfilzomib oxalate

DETAILED DESCRIPTION OF THE INVENTION

The present invention provides an improved commercially viable process for the purification of Carfilzomib, the process of present invention is an easy and cost effective process to implement on industrial scale.

One aspect of the present invention is to provide a process for purification of Carfilzomib of Formula I to reduce an acetamide impurity of Formula II to below 0.10 wt %, comprising the steps of:
(i) dissolving crude Carfilzomib in a first solvent and adding oxalic acid to form Carfilzomib oxalate;
(ii) precipitating said Carfilzomib oxalate;
(iii) reacting said Carfilzomib oxalate with a base in a second solvent to obtain the Carfilzomib Crude Carfilzomib contains undesired impurities including acetamide impurity of formula (II).

The present invention also provides a purified Carfilzomib, wherein an acetamide impurity is present below 0.10% wt of the total weight of Carfilzomib obtained in Step (iii).

Another aspect of the present invention is to produce oxalate salt of Carfilzomib of formula III, which can be used as an intermediate in the preparation of Carfilzomib to reduce the acetamide impurity of formula II below 0.10% in the final Carfilzomib.

Carfilzomib oxalate obtained in the present invention is characterized by X-ray powder diffraction pattern (XRPD) as given in FIG. 1.

Carfilzomib oxalate obtained in the present invention is characterized by X-ray powder diffraction pattern (XRPD) with characteristic peaks at (2 theta±0.2 degree): 4.06, 4.66, 6.99, 8.07, 8.46, 9.30, 10.72 and 14.84.

The first solvent employed for conversion of Carfilzomib to its oxalate salt, i.e Carfilzomib oxalate in step (i) may be an aprotic solvent or a mixture of aprotic solvents such as acetonitrile, tetrahydrofuran or mixture of tetrahydrofurane and acetonitrile, preferably, wherein the first solvent may be a mixture of tetrahydrofuran and acetonitrile.

The ratio of tetrahydrofuran:acetonitrile employed for conversion of Carfilzomib to its oxalate salt, i.e Carfilzomib oxalate in step (i) may be 1:1 to 1:0.5, preferably, 1:0.7 by volume.

The base employed in step (iii) may be selected from triethylamine, diethylamine, ammonia, sodium carbonate, potassium carbonate, sodium bicarbonate, potassium bicarbonate, preferably, wherein the base may be sodium bicarbonate.

The second solvent used in step (iii) may be selected from dichloromethane, ethyl acetate, toluene and chloroform, preferably, wherein the second solvent is dichloromethane.

The reaction temperature of steps (i) to (iii) may be below 35° C.

The Carfilzomib oxalate thus obtained in step (ii) may be precipitated out by cooling down the reaction mixture to below 15° C.

The Carfilzomib oxalate thus obtained in step (ii) is desalted by reacting said Carfilzomib oxalate with a base in a second solvent.

The final Carfilzomib may be isolated by conventional techniques known in the prior art such as crystallization, centrifugation, filtration, precipitation, drying, extraction or combination thereof.

The invention is further illustrated by way of following examples which should not be construed as limiting to the scope of the invention.

EXAMPLES a) Preparation of Carfilzomib Oxalate:

Carfilzomib crude (10 g) and oxalic acid (1.31 g) were dissolved in mixture of Tetrahydrofuran (70 ml) and Acetonitrile (50 ml) and stirred for one hr at 20-25° C. After one hr cool the reaction mixture to 0-10° C. and stirred for three hr followed by filtration of the precipitates so formed give Carfilzomib Oxalate salt.

Carfilzomib oxalate: X-ray powder diffraction pattern (XRPD) with characteristic peaks at (2 theta±0.2 degree): 4.06, 4.66, 6.99, 8.07, 8.46, 9.30, 10.72 and 14.84 b) Preparation of Carfilzomib:

Precipitated carfilzomib oxalate as a wet cake thus obtained in example-1 was dissolved in dichloromethane (100 ml) followed by sodium bicarbonate solution (100 ml) and water (100 ml) washings. Organic layer was concentrated under reduced pressure and product was crystallized in Ethyl Acetate/Methyl tertiary butyl ether mixture (200 ml) (3:7) to afford Carfilzomib (8 g).

Wt: 8 gm
Yield: 80%
Acetamide impurity: 0.04%

The invention claimed is:

1. A process for purification of Carfilzomib of Formula I,

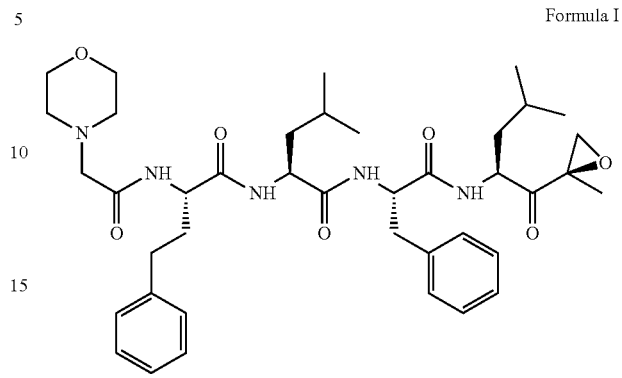

Formula I comprising the steps of:
(i) dissolving crude Carfilzomib in a first solvent and adding oxalic acid, to form Carfilzomib oxalate;
(ii) precipitating said Carfilzomib oxalate;
(iii) reacting said Carfilzomib oxalate with a base in a second solvent, to obtain the Carfilzomib.

2. The process according to claim 1, wherein the Carfilzomib obtained in step (iii) having an acetamide impurity of Formula II, Formula II in an amount less than 0.10 wt % of the total wt of Carfilzomib obtained in step (iii).

3. The process according to claim 1, wherein the first solvent used in step (i) is an aprotic solvent or a mixture of aprotic solvents.

4. The process according to claim 3, wherein the first solvent is a mixture of tetrahydrofuran and acetonitrile.

5. The process according to claim 1, wherein the base employed in step (iii) is selected from triethylamine, diethylamine, ammonia, sodium carbonate, potassium carbonate, sodium bicarbonate, potassium bicarbonate.

6. The process according to claim 1, wherein the second solvent used in step (iii) is selected from dichloromethane, ethyl acetate, toluene and chloroform.

7. The process according to claim 1, wherein steps (i) to (iii) of the reaction are carried out at a temperature range below 35° C.

8. The process according to claim 1, wherein in step (ii) the Carfilzomib oxalate is precipitated by cooling down the reaction mixture to below 15° C.

9. Oxalate salt of Carfilzomib having a structure of Formula (III),

Formula III

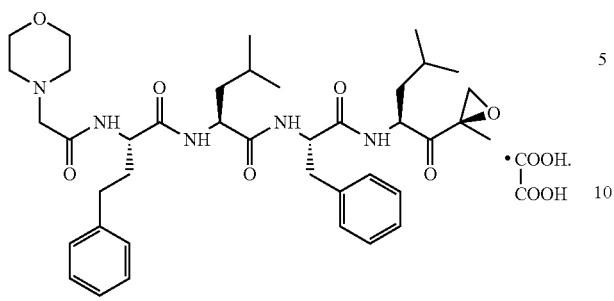

10. Oxalate salt of Carfilzomib according to claim 9, wherein oxalate salt of Carfilzomib has X-ray powder diffraction pattern (XRPD) with characteristic peaks at (2 theta±0.2 degree): 4.06; 4.66; 6.99; 8.07; 8.46; 9.30; 10.72; 14.84.

11. The process according to claim 4, wherein the ratio of tetrahydrofuran:acetonitrile is 1:1 to 1:0.5 by volume.

12. The process according to claim 5, wherein the base is sodium bicarbonate.

13. The process according to claim 6, wherein the second solvent is dichloromethane.

\* \* \* \* \*